United States Patent
Heumann et al.

(10) Patent No.: US 8,604,193 B2
(45) Date of Patent: Dec. 10, 2013

(54) PROCESSES FOR PREPARING HIV REVERSE TRANSCRIPTASE INHIBITORS

(75) Inventors: Stacey Heumann, San Mateo, CA (US); Christopher M. Levins, Redwood City, CA (US); Steven Pfeiffer, Temecula, CA (US); Donald Tang, Millbrae, CA (US)

(73) Assignee: Korea Research Institute of Chemical Technology, Daejeon (KR)

(*) Notice: Subject to any disclaimer, the term of this patent is extended or adjusted under 35 U.S.C. 154(b) by 26 days.

(21) Appl. No.: 13/146,151

(22) PCT Filed: Jan. 26, 2010

(86) PCT No.: PCT/KR2010/000464
§ 371 (c)(1),
(2), (4) Date: Oct. 12, 2011

(87) PCT Pub. No.: WO2010/085128
PCT Pub. Date: Jul. 29, 2010

(65) Prior Publication Data
US 2012/0022257 A1    Jan. 26, 2012

Related U.S. Application Data

(60) Provisional application No. 61/147,206, filed on Jan. 26, 2009.

(51) Int. Cl.
*C07D 239/10*    (2006.01)

(52) U.S. Cl.
USPC ............................ 544/309; 544/313; 544/314

(58) Field of Classification Search
USPC .......................................... 544/309, 313, 314
See application file for complete search history.

(56) References Cited

U.S. PATENT DOCUMENTS

2007/0021450 A1    1/2007    Sklarz et al.

FOREIGN PATENT DOCUMENTS

WO    2007/038859 A1    4/2007
WO    2009/005674 A2    1/2009

OTHER PUBLICATIONS

Bardagi and Rossi (J. Org. Chem. 2008, 73, 4491-4495).*

* cited by examiner

*Primary Examiner* — Noble Jarrell
*Assistant Examiner* — Valerie Rodriguez-Garcia
(74) *Attorney, Agent, or Firm* — Sughrue Mion, PLLC

(57) ABSTRACT

Disclosed is a method for preparing HIV reverse transcriptase inhibitors which inhibit replication of HIV in HIV infected cells, and novel intermediate compounds used therein.

18 Claims, No Drawings

PROCESSES FOR PREPARING HIV REVERSE TRANSCRIPTASE INHIBITORS

CROSS REFERENCE TO RELATED APPLICATIONS

This application is a National Stage of International Application No. PCT/KR2010/000464 filed on Jan. 26, 2010, which claims priority from US Provisional Application No. 61/147,206, filed on Jan. 26, 2009, the contents of all of which are incorporated herein by reference in their entirety.

FIELD OF THE INVENTION

This invention relates to processes and novel intermediate compounds for preparing HIV reverse transcriptase (RT) inhibitors.

BACKGROUND OF THE INVENTION

In recent years, inhibitors of HIV reverse transcriptase (RT) have become an important class of therapeutic agents for inhibition and treatment of HIV infection in human. Compounds that inhibit the enzymatic functions of HIV reverse transcriptase inhibit replication of HIV in infected cells. Such compounds are useful in the prevention or treatment of HIV infection in humans, as demonstrated by known RT inhibitors such as zidovudine, didanosine, zalcitabine, stavudine, lamivudine, emtricitabine, abacavir, tenofovir, nevirapine, delavirdine and efavirenz, the main drugs thus far approved for use in the treatment of AIDS. More recently, Guo, et al., described aroylpyrimidine RT inhibitors in WO2008016522 which is incorporated herein by reference in its entirety.

As with any antiviral therapy, use of RT inhibitors in the treatment of AIDS eventually leads to a virus that is less sensitive to the given drug. Resistance (reduced sensitivity) to these drugs is the result of mutations that occur in the reverse transcriptase segment of the pol gene. Several mutant strains of HIV have been characterized and resistance to known therapeutic agents is believed to be due to mutations in the RT gene. Thus, to be effective, new HIV RT inhibitors must be effective not only against wild-type strains of HIV, but must also demonstrate efficacy against the newly emerging mutant strains that are resistant to the commercially available RT inhibitors. Accordingly, there continues to be a need for new HIV RT inhibitors, and improved methods for preparing new HIV RT inhibitors.

SUMMARY OF THE INVENTION

Accordingly, it is a primary object of the present invention to provide a method for preparing a HIV RT inhibitor compound.

It is another object of the present invention to provide novel intermediate compounds for preparing the HIV RT inhibitor.

In accordance with one aspect of the present invention, there is provided a method for preparing a HIV RT inhibitor compound of Formula (I), which comprises subjecting a compound of Formula (IV) to a reaction with a compound of Formula (V):

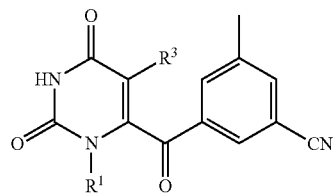

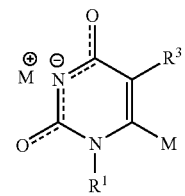

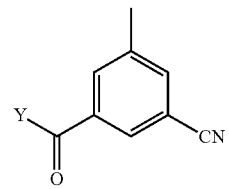

wherein, $R^1$ is alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, heterocyclyl, substituted heterocyclyl, arylalkyl, substituted arylalkyl, heteroarylalkyl, or substituted heteroarylalkyl;

$R^3$ is H, alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, heterocyclyl, substituted heterocyclyl, arylalkyl, substituted arylalkyl, heteroarylalkyl, substituted heteroarylalkyl or —$CHR^7R^8$, $R^7$ and $R^8$ being each independently H, alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, heterocyclyl, substituted heterocyclyl, arylalkyl, substituted arylalkyl, heteroarylalkyl, or substituted heteroarylalkyl;

Y is selected from the group consisting of halogen, cyano, imidazol-1-yl, pyrazol-1-yl, —O—C(O)$R^2$ or —O—C(O)O$R^4$, $R^2$ being H, alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, arylalkyl, substituted arylalkyl, heteroarylalkyl, or substituted heteroarylalkyl, and $R^4$ being alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, arylalkyl, substituted arylalkyl, heteroarylalkyl, or substituted heteroarylalkyl.

In accordance with another aspect of the present invention, there are provided novel intermediate compounds of formulae (II), (III), (V) and (XIII), or salts thereof:

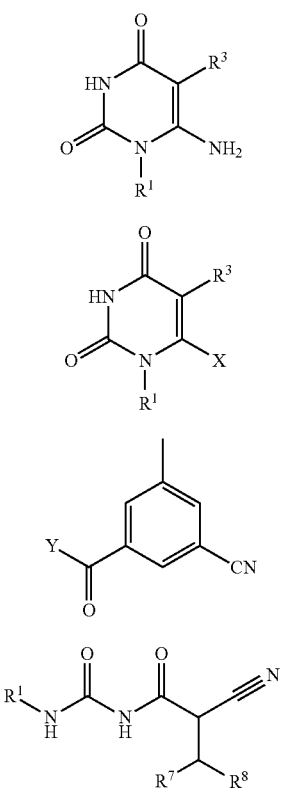

wherein
$R^1$, $R^3$, $R^7$ and $R^8$ are defined as above; and
X is Cl, Br or I.

DETAILED DESCRIPTION OF THE INVENTION

Reference will now be made in detail to certain embodiments of the invention, examples of which are illustrated in the accompanying structures, formulae, and reaction schemes. While the invention will be described in conjunction with the embodiments, it will be understood that they are not intended to limit the invention to those embodiments. On the contrary, the invention is intended to cover all alternatives, modifications, and equivalents, which may be included within the scope of the present invention as defined by the claims.

Unless stated otherwise, the following terms and phrases as used herein are intended to have the following meanings:

When trade names are used herein, applicants intend to independently include the tradename product and the active pharmaceutical ingredient(s) of the tradename product.

In accordance with a convention used in the art,

is used in structural formulas herein to depict the bond that is the point of attachment of the moiety or substituent to the core or backbone structure.

As used herein, the term "a compound of the invention" or "a compound of Formula (I) to Formula (VIII)", etc. refers to a compound of Formula (I) to (VIII) or a pharmaceutically acceptable salt, ester, solvate, stereoisomer or physiologically functional derivative thereof. Similarly, with respect to isolatable intermediates such as for example, compounds of formula (4), the phrase "a compound of formula (number)" means a compound of that formula and pharmaceutically acceptable salts, solvates stereoisomers and physiologically functional derivatives thereof.

As used herein, the term "alkyl" refers to hydrocarbon containing normal, secondary, tertiary or cyclic carbon atoms. For example, an alkyl group can have 1 to 20 carbon atoms (i.e, $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (1-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)$ $CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)$ $(CH_2CH_2CH_3)$), 2-methyl-2-pentyl (—$C(CH_3)_2$ $CH_2CH_2CH_3$), 3-methyl-2-pentyl (—$CH(CH_3)CH(CH_3)$ $CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C$ $(CH_3)_2CH(CH_3)_2$), 3,3-dimethyl-2-butyl (—$CH(CH_3)C$ $(CH_3)_3$, and octyl (—$(CH_2)_7CH_3$).

As used herein, the term "alkoxy" refers to a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu) and the like.

As used herein, the term "haloalkyl" refers to an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

As used herein, the term "alkenyl" refers to a hydrocarbon containing normal, secondary, tertiary or cyclic carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

As used herein, the term "alkynyl" refers to a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne), or 2 to 6 carbon atoms (i.e., $C_2$-$C_6$ alkynyl).

Examples of suitable alkynyl groups include, but are not limited to, acetylenic (—C≡CH), propargyl (—CH$_2$C≡CH), and the like.

As used herein, the term "alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Examples of alkylene radical include, but are not limited to, methylene (—CH$_2$—), 1,1-ethyl (—CH(CH$_3$)—), 1,2-ethyl (—CH$_2$CH$_2$—), 1,1-propyl (—CH(CH$_2$CH$_3$)—), 1,2-propyl (—CH$_2$CH(CH$_3$)—), 1,3-propyl (—CH$_2$CH$_2$CH$_2$—), 1,4-butyl (—CH$_2$CH$_2$CH$_2$CH$_2$—), and the like.

As used herein, the term "alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Examples of alkenylene radical include, but are not limited to, 1,2-ethylene (—CH═CH—).

As used herein, the term "alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Examples of alkynylene radical include, but are not limited to, acetylene (—C≡C—), propargyl (—CH$_2$C≡C—), and 4-pentynyl (—CH$_2$CH$_2$CH$_2$C≡CH—).

As used herein, the term "aryl" refers to an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Examples of aryl group include, but are not limited to, radicals derived from benzene (e.g., phenyl), substituted benzene, naphthalene, anthracene, biphenyl, and the like.

As used herein, the term "arylalkyl" refers to an acyclic alkyl radical in which one of the hydrogen atoms bonded to a carbon atom, typically a terminal or sp$^3$ carbon atom, is replaced with an aryl radical. For example, the arylalkyl group can comprise 6 to 20 carbon atoms, e.g., the alkyl moiety is 1 to 6 carbon atoms and the aryl moiety is 6 to 14 carbon atoms. Examples of arylalkyl groups include, but are not limited to, benzyl, 2-phenylethan-1-yl, naphthylmethyl, 2-naphthylethan-1-yl, naphthobenzyl, 2-naphthophenylethan-1-yl and the like.

As used herein, the term "arylalkenyl" refers to an acyclic alkenyl radical in which one of the hydrogen atoms bonded to a carbon atom, typically a terminal or sp$^3$ carbon atom, but also a sp$^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 6 to 20 carbon atoms, e.g., the alkenyl moiety is 1 to 6 carbon atoms and the aryl moiety is 6 to 14 carbon atoms.

As used herein, the term "arylalkynyl" refers to an acyclic alkynyl radical in which one of the hydrogen atoms bonded to a carbon atom, typically a terminal or sp$^a$ carbon atom, but also a sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 6 to 20 carbon atoms, e.g., the alkynyl moiety is 1 to 6 carbon atoms and the aryl moiety is 6 to 14 carbon atoms.

As used herein, the term "substituted" in reference to alkyl, alkylene, aryl, arylalkyl, heterocyclyl, etc., for example, "substituted alkyl", "substituted alkylene", "substituted aryl", "substituted arylalkyl", "substituted heterocyclyl", and "substituted carbocyclyl" refers to alkyl, alkylene, aryl, arylalkyl, heterocyclyl, carbocyclyl respectively, in which one or more hydrogen atoms are each independently replaced with a non-hydrogen substituent. Examples of substituent include, but are not limited to, —X$^a$, —R, —O$^-$, ═O, —OR, —SR, —S$^-$, —NR$_2$, —N$^+$R$_3$, ═NR, —CX$^a_3$, —CN, —OCN, —SCN, —N═C═O, —NCS, —NO, —NO$_2$, ═N$_2$, —N$_3$, —NHC(═O)R, —C(═O)R, —C(═O)NRR—S(═O)$_2$O$^-$, —S(═O)$_2$OH, —S(═O)$_2$R, —OS(═O)$_2$OR, —S(═O)$_2$NR$_2$, —S(═O)R, —OP(═O)(OR)$_2$, —N(═O)(OR)$_2$, —N(═O)(O$^-$)$_2$, —N(═O)(OH)$_2$, —N(O)(OR)(O$^-$), —C(═O)R, —C(═O)X$^a$, —C(S)R, —C(O)OR, —O—C(O)R, —C(O)O$^-$, —C(S)OR, —C(O)SR, —C(S)SR, —C(O)NRR, —C(S)NRR, —C(═NR)NRR, where each X$^a$ is independently a halogen: F, Cl, Br, or I; and each R is independently H, alkyl, aryl, arylalkyl, a heterocycle, or a protecting group or prodrug moiety. Alkylene, alkenylene, and alkynylene groups may also be similarly substituted.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds disclosed herein should be selected in order to provide a compound which is sufficiently stable to provide a pharmaceutically useful compound which can be formulated into an acceptably stable pharmaceutical composition or a sufficiently stable intermediate that can be used in a method of preparing a compound of the invention. Compounds which have such stability are contemplated as falling within the scope of the present invention.

As used herein, "heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

The terms "heterocycle" or "heterocyclyl" as used herein includes by way of example and not limitation those heterocycles described in Paquette, Leo A.; *Principles of Modern*

*Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., hetero aromatic rings). Substituted heterocyclyls include, for example, heterocyclic rings substituted with any of the substituents disclosed herein including carbonyl groups.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl, and the like.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or -carboline. Still more typically, nitrogen bonded heterocycles include 1-aziridyl, 1-azetedyl, 1-pyrrolyl, 1-imidazolyl, 1-pyrazolyl, and 1-piperidinyl.

As used herein, the term "heterocyclene" refers to a heterocycle as defined herein having two monovalent radical centers derived by the removal of two hydrogen atoms from the same carbon atom or two different carbon or nitrogen atoms of a parent heterocycle.

As used herein, the term "heterocyclylalkyl" refers to an acyclic alkyl radical in which one of the hydrogen atoms bonded to a carbon atom, typically a terminal or $sp^3$ carbon atom, is replaced with a heterocyclyl radical (i.e., a heterocyclyl-alkylene-moiety). Examples of heterocyclyl alkyl group include, but are not limited to heterocyclyl-$CH_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 6 to 20 carbon atoms, e.g., the alkyl portion of the arylalkyl group is 1 to 6 carbon atoms and the heterocyclyl moiety is 5 to 14 carbon atoms. Examples of heterocyclylalkyl include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

As used herein, the term "heterocyclylalkenyl" refers to an acyclic alkenyl radical in which one of the hydrogen atoms bonded to a carbon atom, typically a terminal or $sp^3$ carbon atom, but also a $sp^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 6 to 20 carbon atoms, e.g., the alkenyl portion of the heterocyclyl alkenyl group is 1 to 6 carbon atoms and the heterocyclyl moiety is 5 to 14 carbon atoms.

As used herein, the term "heterocyclylalkynyl" refers to an acyclic alkynyl radical in which one of the hydrogen atoms bonded to a carbon atom, typically a terminal or $sp^3$ carbon atom, but also a sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 6 to 20 carbon atoms, e.g., the alkynyl portion of the heterocyclyl alkynyl group is 1 to 6 carbon atoms and the heterocyclyl moiety is 5 to 14 carbon atoms.

As used herein, the term "heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

As used herein, the term "carbocycle" or "carbocyclyl" refers to a saturated, partially unsaturated or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl.

As used herein, the term "carbocyclene" refers to a saturated (i.e., cycloalkyl), partially unsaturated (e.g., cycloakenyl, cycloalkadienyl, etc.) or aromatic radical as described for "carbocycle" having two monovalent radical centers derived by the removal of two hydrogen atoms from the same or two different carbon atoms of a parent carbocycle.

As used herein, the term "arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, etc. In addition, any of the alkylene moieties in the general formulae above can be further substituted with any of the substituents defined or exemplified herein.

As used herein, the term "heteroarylalkyl" refers to an alkyl group, as defined herein, in which a hydrogen atom has been replaced with a heteroaryl group as defined herein. Non-limiting examples of heteroaryl alkyl include —$CH_2$-pyridinyl, —$CH_2$-pyrrolyl, —$CH_2$-oxazolyl, —$CH_2$-indolyl, —$CH_2$-isoindolyl, —$CH_2$-purinyl, —$CH_2$-furanyl, —$CH_2$-thienyl, —$CH_2$-benzofuranyl, —$CH_2$-benzothiophenyl, —$CH_2$-carbazolyl, —$CH_2$-imidazolyl, —$CH_2$-thiazolyl, —$CH_2$-isoxazolyl, —$CH_2$-pyrazolyl, —$CH_2$-isothiazolyl, —$CH_2$-quinolyl, —$CH_2$-isoquinolyl, —$CH_2$-pyridazyl, —$CH_2$-pyrimidyl, —$CH_2$-pyrazyl, —$CH(CH_3)$-pyridinyl, —$CH(CH_3)$-pyrrolyl, —$CH(CH_3)$-oxazolyl, —$CH(CH_3)$-indolyl, —$CH(CH_3)$-isoindolyl, —$CH(CH_3)$-purinyl, —$CH(CH_3)$-furanyl, —$CH(CH_3)$-thienyl, —$CH(CH_3)$-benzofuranyl, —$CH(CH_3)$-benzothiophenyl, —$CH(CH_3)$-carbazolyl, —$CH(CH_3)$-imidazolyl, —$CH(CH_3)$— thiazolyl, —$CH(CH_3)$-isoxazolyl, —$CH(CH_3)$-pyrazolyl, —$CH(CH_3)$-isothiazolyl, —$CH(CH_3)$-quinolyl, —$CH(CH_3)$-isoquinolyl, —$CH(CH_3)$-pyridazyl, —$CH(CH_3)$-pyrimidyl, —$CH(CH_3)$-pyrazyl, etc.

As used herein, the terms "phosphonate" and "phosphonate group" mean a functional group or moiety within a molecule that comprises at least one phosphorus-carbon bond, and at least one phosphorus-oxygen double bond. The phosphorus atom is further substituted with oxygen, sulfur, and nitrogen substituents. As defined herein, "phosphonate" and "phosphonate group" include molecules with phosphonic acid, phosphonic monoester, phosphonic diester, phosphonamidate, phosphondiamidate, and phosphonthioate functional groups.

As used herein, the term "linker" or "link" refers to a chemical moiety comprising a covalent bond or a chain or group of atoms that covalently attaches a phosphonate or phosphinate group to a drug. Linkers which include moieties such as: repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

As used herein, the term "Optionally substituted" refers to a particular moiety of the compound of Formula (I-XI) (e.g., an optionally substituted aryl group) refers to a moiety having 0, 1, 2, or more substituents.

As used herein, the term "ester thereof" refers to any ester of a compound in which any of the —COOH functional groups of the molecule is replaced by a —COOR function, or any of the —OH functional groups of the molecule is replaced with a —O—C(O)R in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The term "ester thereof" includes but is not limited to pharmaceutically acceptable esters thereof.

As used herein, the term "salt thereof" refers to any acid and/or base addition salt of a compound according to the invention; preferably a pharmaceutically acceptable salt thereof.

As used herein, the term "Pharmaceutically acceptable salt" refers to a salt of a compound which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. Where applicable and compatible with the chemical properties of the compound of formula (I), (II), (III), etc., the term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19.

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space. Stereoisomers include, e.g. diastereomers and enantiomers as described herein.

As used herein, the term "diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

As used herein, the term "enantiomers" refer to two stereoisomers of a compound which are non-superimposable mirror images of one another.

Stereochemical definitions and conventions used herein generally follow S, N. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

As used herein, the term "nitrosating reagent" refers to a reagent that converts a primary amine (—$NH_2$ group) to a diazonium group (—$N_2^+$). Non-limiting examples of nitrosating reagents are alkali metal nitrites, alkaline earth nitrites and alkyl or substituted alkyl nitrite esters.

The modifier "about" used in connection with a quantity is inclusive of the stated value and has the meaning dictated by the context (e.g., includes the degree of error associated with measurement of the particular quantity).

As used herein, the term "transition metal" refers to groups 3-12 of the periodic table. This would expressly include zinc, cadmium and mercury. Transition metals would include the "noble metals" ruthenium, rhodium, palladium, osmium, iridium, platinum and gold.

One skilled in the art will recognize that the pyrimidinedione rings of the compounds of Formula (I) to (IV) can exist in tautomeric forms. For example, but not by way of limitation, structures (a) and (b) can have equivalent tautomeric forms as shown below:

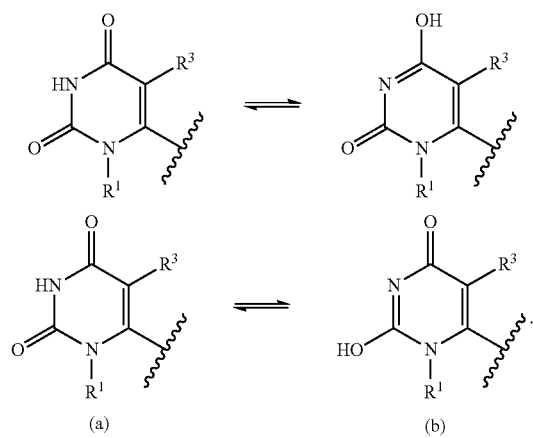

Similarly, the salt forms of these pyrimidinediones can have equivalent tautomeric forms as shown below:

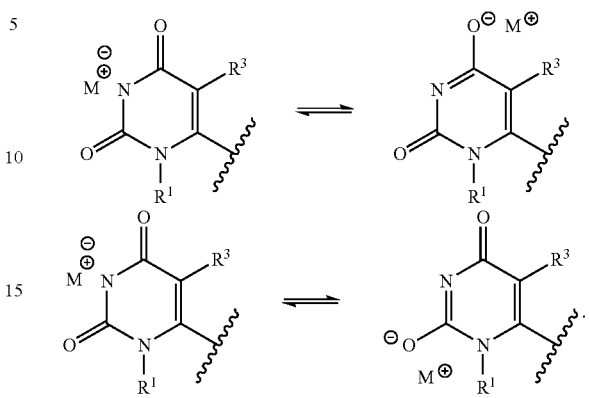

In another representation, the multiple tautomeric salt forms could be represented by Formula (c):

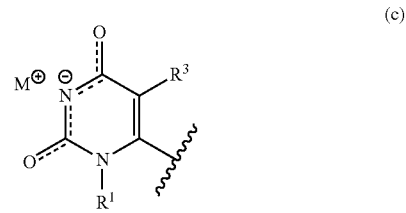

All possible tautomeric forms of the pyrimidinediones and salts thereof, of all of the embodiments are within the scope of the invention.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene and Peter G. M. Wuts (John Wiley & Sons, Inc., New York, 1999, ISBN 0-471-16019-9) ("Greene"). See also Kocienski, Philip J.; *Protecting Groups* (Georg Thieme Verlag Stuttgart, New York, 1994), both of which are herein incorporated by reference in their entirety for all purposes. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

In accordance with one aspect of the present invention (method (e)), there is provided a method for preparing a HIV RT inhibitor compound of Formula (I), which comprises subjecting the compound of Formula (IV) to a reaction with a compound of Formula (V):

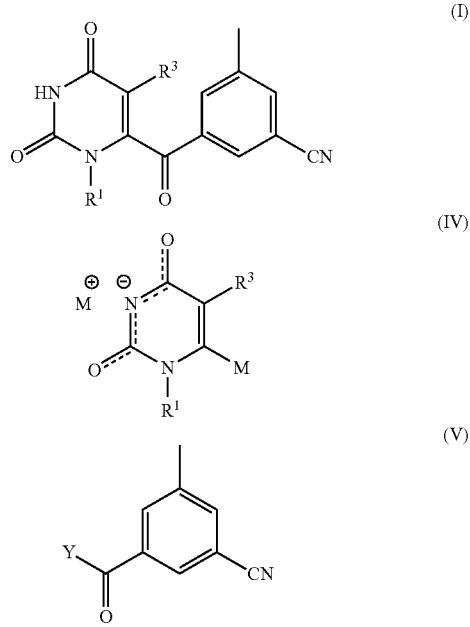

wherein, $R^1$ is alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, heterocyclyl, substituted heterocyclyl, arylalkyl, substituted arylalkyl, heteroarylalkyl, or substituted heteroarylalkyl;

$R^3$ is H, alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, heterocyclyl, substituted heterocyclyl, arylalkyl, substituted arylalkyl, heteroarylalkyl, substituted heteroarylalkyl or —$CHR^7R^8$, $R^7$ and $R^8$ being each independently H, alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, heterocyclyl, substituted heterocyclyl, arylalkyl, substituted arylalkyl, heteroarylalkyl, or substituted heteroarylalkyl;

M is $MgX^1$ or $L^1$, $X^1$ being halogen; and

Y is selected from the group consisting of halogen, cyano, imidazol-1-yl; pyrazol-1-yl, —O—C(O)$R^2$ or —O—C(O)O$R^4$, $R^2$ being H, alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, arylalkyl, substituted arylalkyl, heteroarylalkyl, or substituted heteroarylalkyl, and $R^4$ being alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, arylalkyl, substituted arylalkyl, heteroarylalkyl, or substituted heteroarylalkyl.

In a particular embodiment, $R^1$ is alkyl, alkenyl, alkynyl, aryl, substituted aryl, heteroaryl, substituted heteroaryl, arylalkyl, substituted arylalkyl, heteroarylalkyl, or substituted heteroarylalkyl. In a particular embodiment, $R^1$ and $R^3$ are each independently alkyl groups. In another particular embodiment, $R^3$ is isopropyl. In yet another embodiment, $R^1$ is ethyl. In still another embodiment, $R^1$ is ethyl and $R^3$ is isopropyl.

In one embodiment, Y is halogen. In another embodiment, Y is Cl. In another embodiment, Y is cyano. In another embodiment, Y is imidazol-1-yl. In another embodiment, Y is pyrazol-1-yl. In another embodiment, Y is —O—C(O)$R^2$. In another embodiment, Y is —O—C(O)O$R^4$.

In a preferred embodiment, $R^1$ and $R^3$ is each independently alkyl and Y is imidazol-1-yl or Cl. In another preferred embodiment, $R^1$ is ethyl, $R^3$ is isopropyl and Y is imidazol-1-yl or Cl.

In one embodiment, the mole ratio of the compound of Formula (IV) to the compound of Formula (V) is about 1:1 to about 1:3, preferably about 1:1 to about 1:1.5. Typically, the compound of Formula (IV) is treated with the compound of Formula (V) in an aprotic solvent such as, but not limited to, THF or ether at about −30 to about 25° C. for about 30 minutes to about 24 hours.

In accordance with another aspect of the present invention (method (d-1)), there is provided a method for preparing the compound of Formula (IV) which comprises treating the compound of Formula (III) with an organomagnesium or an organolithium reagent:

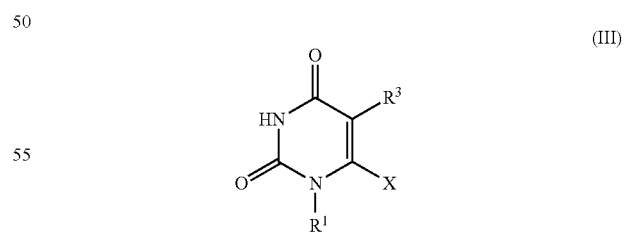

wherein $R^1$ and $R^3$ are defined as above; and

X is Cl, Br or I.

In a particular embodiment, $R^1$ is independently alkyl, alkenyl, alkynyl, aryl, substituted aryl, heteroaryl, substituted heteroaryl, arylalkyl, substituted arylalkyl, heteroarylalkyl, or substituted heteroarylalkyl. In another particular embodiment, $R^1$ and $R^3$ are each independently alkyl groups. In another particular embodiment, $R^3$ is isopropyl. In yet another embodiment, $R^1$ is ethyl. In still another embodiment, $R^1$ is ethyl and $R^3$ is isopropyl.

In another aspect of the invention (method (d-2)), the compound of Formula (IV), wherein M is $MgX^1$, $X^1$ being halogen, is prepared by treating the compound of Formula (III) with an organomagnesium reagent.

Typically, the transmetalation reaction is performed in a suitable aprotic solvent at about −78° C. to abut 50° C. for about 5 minutes to 24 hours. Non-limiting examples of suitable aprotic solvents include THF, dioxane and ether.

In one embodiment, the mole ratio of the compound of Formula (III) to organomagnesium reagent is about 1:1 to about 1:3, preferably about 1:2. In one embodiment, the organomagnesium reagent comprises an alkylmagnesium chloride, bromide, or iodide. In another embodiment, the organomagnesium reagent comprises 2-propylmagnesium chloride.

In another embodiment, the organomagnesium reagent comprises 2-propylmagnesium chloride and the transmetalation reaction is carried out in the presence of lithium chloride. In another embodiment, the organomagnesium reagent comprises 2-propylmagnesium chloride, the transmetalation reaction is carried out in the presence of lithium chloride, and the mole ratio of 2-propylmagnesium chloride to lithium chloride is about 1:1. In a preferred embodiment, the organomagnesium reagent comprises 2-propylmagnesium chloride, the transmetalation reaction is carried out in the presence of lithium chloride, the mole ratio of 2-propylmagnesium chloride to lithium chloride is about 1:1, and the X of Formula (III) is Br or I.

In a particular embodiment, $R^1$ is independently alkyl, alkenyl, alkynyl, aryl, substituted aryl, heteroaryl, substituted heteroaryl, arylalkyl, substituted arylalkyl, heteroarylalkyl, or substituted heteroarylalkyl. In another particular embodiment, $R^1$ and $R^3$ are each independently alkyl groups. In another particular embodiment, $R^3$ is isopropyl. In yet another embodiment, $R^1$ is ethyl. In still another embodiment, $R^1$ is ethyl and $R^3$ is isopropyl.

In another aspect of the invention (method (d-3)), the compound of Formula (IV), wherein M is $MgX^1$, $X^1$ being halogen, is prepared by treating a compound of Formula (III) with more than one organomagnesium reagent.

One skilled in the art will recognize that the reactive NH bond of the compound of Formula (III) will consume one mole equivalent of the organomagnesium reagent. The organomagnesium reagent consumed may be different from the organomagnesium reagent that produces the transmetalation reaction. For example, but not by way of limitation, treating the compound of Formula (III) with one mole equivalent of methylmagnesium chloride would neutralize the NH bond of the compound of Formula (III) by forming a magnesium salt and the Cl, Br, or I group of the compound of Formula (III) could then be transmetalated with another organomagnesium reagent such as 2-propylmagnesium chloride or 2-propylmagnesium chloride and lithium chloride.

Typically, the transmetalation reaction is performed in a suitable aprotic solvent at about −78° C. to abut 50° C. for about 5 minutes to 24 hours. Non-limiting examples of suitable aprotic solvents include THF, dioxane and ether.

In one embodiment, the compound of Formula (IV) is prepared by treating the compound of Formula (III) with about one mole equivalent of a first organomagnesium reagent followed by treatment with a second organomagnesium reagent. In one embodiment, the mole ratio of the first organometallic reagent to the molecule of Formula (III) is about 1:1 and the mole ratio of the second organomagnesium reagent to the compound of Formula (III) is about 1:0.8 to about 1:2, preferably about 1:1. In one embodiment, the first organomagnesium reagent comprises an alkylmagnesium chloride, bromide, or iodide. In another embodiment, the first organomagnesium reagent comprises methylmagnesium chloride. In another embodiment, the second organomagnesium reagent comprises an alkylmagnesium chloride, bromide, or iodide. In another embodiment, the second alkylmagnesium reagent comprises 2-propylmagnesium chloride. In another embodiment, the second organomagnesium reagent comprises 2-propylmagnesium chloride and the transmetalation reaction using the second organomagnesium reagent is carried out in the presence of lithium chloride, and the mole ratio of 2-propylmagnesium chloride to lithium chloride is about 1:1. In a preferred embodiment, the first organomagnesium reagent is methylmagnesium chloride and the second organomagnesium reagent comprises 2-propylmagnesium chloride. In another preferred embodiment the first organomagnesium reagent is methylmagnesium chloride, the second organomagnesium reagents is 2-propylmagnesium chloride, the transmetalation reaction using the second organomagnesium reagent is carried out in the presence of lithium chloride, and the mole ratio of 2-propylmagnesium chloride to lithium chloride is about 1:1. In another preferred embodiment the first organomagnesium reagent is methylmagnesium chloride, the second organomagnesium reagents is 2-propylmagnesium chloride, the transmetalation reaction using the second organomagnesium reagent is carried out in the presence of lithium chloride, the mole ratio of 2-propylmagnesium chloride to lithium chloride is about 1:1, and the X of Formula (III) is Br or I.

In a particular embodiment, $R^1$ is independently alkyl, alkenyl, alkynyl, aryl, substituted aryl, heteroaryl, substituted heteroaryl, arylalkyl, substituted arylalkyl, heteroarylalkyl, or substituted heteroarylalkyl. In another particular embodiment, $R^1$ and $R^3$ are each independently alkyl groups. In another particular embodiment, $R^3$ is isopropyl. In yet another embodiment, $R^1$ is ethyl. In still another embodiment, $R^1$ is ethyl and $R^3$ is isopropyl. In another preferred embodiment the first organomagnesium reagent is methylmagnesium chloride, the second organomagnesium reagents is 2-propylmagnesium chloride, the transmetalation reaction using the second organomagnesium reagent is carried out in the presence of lithium chloride, the mole ratio of 2-propylmagnesium chloride to lithium chloride is about 1:1, the X of Formula (III) is Br or I, and $R^1$ and $R^3$ are each independently alkyl groups.

In another aspect of the invention (method (d-4)), the compound of Formula (IV), wherein M is Li, is prepared by treating a compound of Formula (III) with an organolithium reagent.

Typically, the transmetalation reaction is performed in a suitable aprotic solvent at about −100° C. to about 20° C. for about 5 minutes to 24 hours. Non-limiting examples of suitable aprotic solvents include THF and ether.

In one embodiment, the mole ratio of the compound of Formula (III) to organolithium reagent is about 1:1 to about 1:3, preferably about 1:2. In one embodiment, the organolithium reagent comprises an alkyllithium reagent such as n-butyllithium, iso-butyllithium, and tert-butyllithium. In a preferred embodiment, the organolithium reagent comprises an alkyllithium reagent and the X of Formula (III) is Br or I. In a particular embodiment, $R^1$ is independently alkyl, alkenyl, alkynyl, aryl, substituted aryl, heteroaryl, substituted heteroaryl, arylalkyl, substituted arylalkyl, heteroarylalkyl, or substituted heteroarylalkyl. In another particular embodiment, $R^1$ and $R^3$ are each independently alkyl groups. In another particular embodiment, $R^3$ is isopropyl. In yet another embodiment, $R^1$ is ethyl. In still another embodiment, $R^1$ is ethyl and $R^3$ is isopropyl.

In accordance with another aspect of the present invention (method (c)), there is provided a method for preparing the compound of Formula (III) which comprises treating the compound of Formula (II) with a nitrosating reagent in the presence of a transition metal halide:

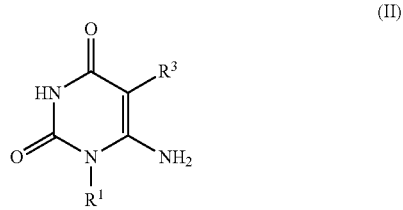

wherein $R^1$ and $R^3$ are defined as above.

In a particular embodiment, $R^1$ is independently alkyl, alkenyl, alkynyl, aryl, substituted aryl, heteroaryl, substituted heteroaryl, arylalkyl, substituted arylalkyl, heteroarylalkyl, or substituted heteroarylalkyl. In a particular embodiment, $R^1$ and $R^3$ are each independently alkyl groups. In another particular embodiment, $R^3$ is isopropyl. In yet another embodiment, $R^1$ is ethyl. In still another embodiment, $R^1$ is ethyl and $R^3$ is isopropyl.

Non-limiting examples of nitrosating reagents include alkali metal nitrites, alkaline earth nitrites, and nitrite esters having alkyl group or substituted alkyl group. In one embodiment, the alkali metal nitrite is lithium, sodium or potassium nitrite. In a preferred embodiment the alkali metal nitrite is sodium nitrite. In one embodiment the alkyl or substituted alkyl nitrite ester is tert-butyl or isoamyl nitrite. The mole ratio of the compound of Formula (II) to nitrosating reagent is about 1:1 to about 1:4; preferably about 1:1 to about 1:2. In one embodiment, the transition metal halide comprises a transition metal chloride, bromide, iodide and a mixture thereof. The transition metal chloride, bromide or iodide is $CuCl_2$, $CuBr_2$ or $CuI_2$, respectively. In a preferred embodiment, the transition metal bromide is $CuBr_2$. The mole ratio of the compound of Formula (II) to transition metal halide is about 1:1 to about 1:5, preferably about 1:1 to about 1:2.

In another embodiment, the compound Formula (III) is obtained from the compound of Formula (II) in about 50 to about 100% yield; preferably in about 80 to about 100% yield.

In another aspect of the invention, the compound of Formula (I) is obtained from the compound of Formula (III) in the reaction sequence described above in about 30% to about 100% yield, preferably in about 50% to about 100% yield.

In another aspect of the invention (method (b)), the compound of Formula (II) is prepared by subjecting a compound of Formula (VI) to a reaction with a compound of Formula (VII) in the presence of a suitable base, as shown in Scheme 1:

Scheme 1

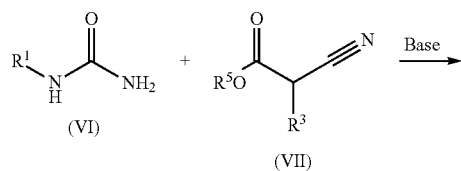

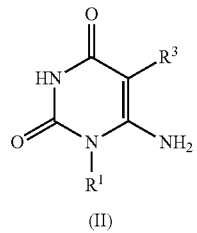

wherein,
$R^1$ and $R^3$ are as defined above;
$R^5$ is alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, heterocyclyl, substituted heterocyclyl, arylalkyl, substituted arylalkyl, heteroarylalkyl, substituted heteroarylalkyl or $Si(R^6)_3$, $R^6$ being each independently alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, heterocyclyl, substituted heterocyclyl, arylalkyl, substituted arylalkyl, heteroarylalkyl, or substituted heteroarylalkyl.

Typically, the preparation is performed in a suitable solvent such as, but not limited to, an alkyl or substituted alkyl alcohol at about 20° C. to about 120° C. for about 1 hour to about 48 hours. Non-limiting examples of alkyl or substituted alkyl alcohols are methanol, ethanol, propanol, isopropanol, butanol, tert-butanol, isobutanol, and isoamyl alcohol. Typically, the mole ratio of the compound of Formula (VII) to the compound of Formula (VI) is about 1:1 to about 1:4; preferably about 1:1 to about 1:1.1. In one embodiment of this aspect, the suitable base is an alkali metal alkoxide. Non-limiting examples of alkali metal alkoxides include lithium, sodium, and potassium salts of methanol, ethanol, propanol, isopropanol, butanol, tert-butanol, isobutanol, and isoamyl alcohol. In a preferred embodiment, the alkali metal alkoxide is sodium methoxide or sodium ethoxide. Typically, the mole ratio of the compound of Formula (VII) to suitable base is about 1:1 to about 1:4; preferably about 1:1.1 to about 1:1.5. In a particular embodiment, $R^1$ is independently alkyl, alkenyl, alkynyl, aryl, substituted aryl, heteroaryl, substituted heteroaryl, arylalkyl, substituted arylalkyl, heteroarylalkyl, or substituted heteroarylalkyl and the alkali metal alkoxide is sodium methoxide or sodium ethoxide. In a preferred embodiment, the alkali metal alkoxide is sodium methoxide or sodium ethoxide and $R^1$ and $R^3$ are each independently alkyl groups. In another preferred embodiment, the alkali metal alkoxide is sodium methoxide or sodium ethoxide; $R^1$ is ethyl and $R^3$ is isopropyl. In another preferred embodiment, the compound of Formula (II) is obtained from the compound of Formula (VII) in about 35% to about 100% yield; preferably in about 50% to about 100% yield. In another preferred embodiment, the compound of Formula (II) is obtained from the compound of Formula (VII), wherein each $R^1$ and $R^3$ is independently alkyl, in about 35% to about 100% yield; preferably in about 50% to about 100% yield.

In another aspect of the invention (method (a)), a compound of Formula (II), wherein $R^3$ is $CHR^7R^8$ is prepared in several steps comprising:
(a-1) treating a compound of Formula (XI) with a compound selected from the group consisting of compounds of formulae (XII) to (XIV), in the presence of a reducing agent thereby forming a compound of Formula (VIII), and (a-2) subjecting the compound of Formula (VIII) to a reaction with a compound of Formula (IX) in the presence of a compound of Formula (X):

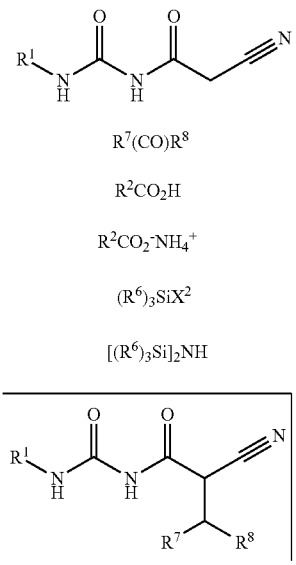

$R^7(CO)R^8$ (XII)

$R^2CO_2H$ (XIII)

$R^2CO_2^-NH_4^+$ (XIV)

$(R^6)_3SiX^2$ (IX)

$[(R^6)_3Si]_2NH$ (X)

(VIII)

Wherein,
$R^1$, $R^2$, $R^6$, $R^7$ and $R^8$ are defined as above, and
$X^2$ is halogen.

In another aspect of the invention (method (a-2)), the compound of Formula (II), wherein $R^3$ is $CHR^7R^8$, is prepared by reacting a compound of Formula (VIII) (e.g., Papesch, V.; *J. Org. Chem.* 1951, 1879) with a compound of Formula (IX) in the presence of a compound of Formula (X), as shown in Scheme 2 (Fulle, F; *Heterocycles* 2000, 347-351).

Scheme 2

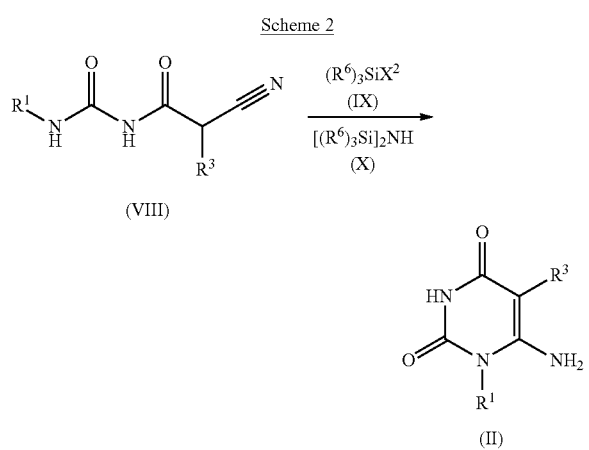

Wherein, $R^1$, $R^2$, $R^6$, $R^7$, $R^8$ and $X^2$ are defined as above.

In one embodiment, the mole ratio of the compound of Formula (VIII) to $(R^6)_3SiX^2$ of Formula (IX) is about 1:1 to about 100:1; preferably about 9:1 to about 100:1. Typically, the treatment is heated to about 20° C. to about 150° C. for about one to about 48 hours.

In one embodiment, each $R^6$ is methyl and $X^2$ is Cl. In a preferred embodiment, $R^1$ and $R^3$ of Formula (VIII) are each independently alkyl groups. In a particular embodiment, $R^1$ is independently alkyl, alkenyl, alkynyl, aryl, substituted aryl, heteroaryl, substituted heteroaryl, arylalkyl, substituted arylalkyl, heteroarylalkyl, or substituted heteroarylalkyl. In another preferred embodiment, $R^1$ is ethyl. In another preferred embodiment, $R^3$ is $CHR^7R^8$. In another preferred embodiment, $R^3$ is isopropyl. In another preferred embodiment, $R^1$ is ethyl and $R^3$ is isopropyl. In another preferred embodiment, $R^1$ is alkyl, $R^3$ is $CHR^7R^8$, each $R^6$ is methyl and $X^2$ is Cl. In another preferred embodiment, $R^1$ is ethyl, $R^3$ is isopropyl, each $R^6$ is methyl and $X^2$ is Cl.

In another embodiment, the compound of Formula (II) is obtained from the compound of Formula (VIII) in about 30% to about 100% yield; preferably in about 40% to about 100% yield. In another embodiment, the compound of Formula (II) is obtained from the compound of Formula (VIII), wherein $R^1$ is alkyl, $R^3$ is $CHR^7R^8$, and each $R^6$ is methyl, in about 30% to about 100% yield; preferably in about 40% to about 100% yield In another aspect of the invention (method (a-1)), the compound of Formula (VIII) is prepared by subjecting a compound of Formula (XI) to a reaction with a compound selected from the group consisting of compounds of Formulae (XII) to (XIV), in the presence of a suitable reducing agent, as shown in Scheme 3:

Scheme 3

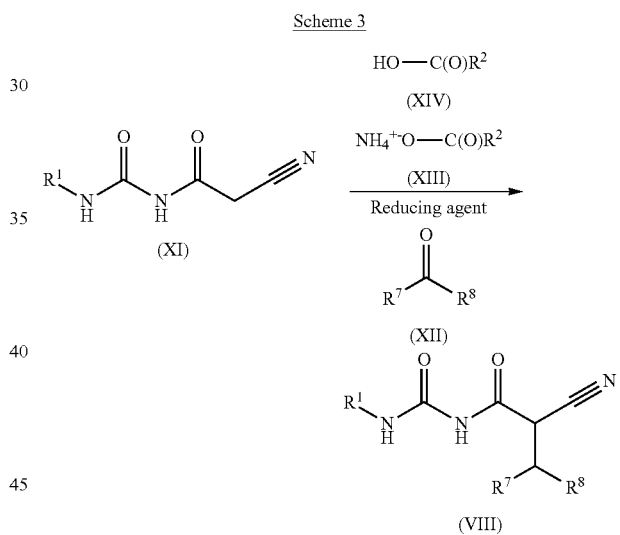

wherein $R^1$, $R^2$, $R^7$ and $R^8$ are defined as above.

In one embodiment, the suitable reducing agent is a transition metal catalyst and $H_2$. In a preferred embodiment, the suitable reducing agent is a noble metal catalyst, for example palladium or platinum on carbon, and $H_2$. In another preferred embodiment, the suitable reducing agent is palladium on carbon (Pd/C) and $H_2$. When the reducing agent comprises $H_2$, the $H_2$ is used at about one to about five atmospheres of pressure, preferably with $H_2$ at about atmospheric pressure to about 50 psi of pressure, more preferably with $H_2$ at about atmospheric pressure to about 20 psi of pressure.

Typically, the treatment is conducted in a suitable solvent at about −10° C. to about 65° C. for about 30 minutes to about 48 hours. Non-limiting examples of suitable solvents comprise ethanol, isopropanol, THF and dioxane.

In one embodiment each $R^1$, $R^2$, $R^7$ and $R^8$ is independently alkyl. In a particular embodiment, $R^1$ is independently alkyl, alkenyl, alkynyl, aryl, substituted aryl, heteroaryl, substituted heteroaryl, arylalkyl, substituted arylalkyl, heteroarylalkyl, or substituted heteroarylalkyl. In another embodiment R¹ is ethyl. In another embodiment, each R⁷ and R⁸ is methyl. In a preferred embodiment, R¹ is ethyl, and each R², R⁷ and R⁸ is methyl.

In another embodiment, the compound of Formula (VIII) is obtained from the compound of Formula (XI) in about 50% to about 100% yield; preferably in about 80% to about 100% yield. In another preferred embodiment, each R¹, R², R⁷ and R⁸ is independently alkyl and the compound of Formula (VIII) is obtained from the compound of Formula (XI) in about 50% to about 100% yield; preferably in about 80% to about 100% yield.

In another aspect of the invention, a compound of Formula (III) is converted to a compound of Formula (IV) by at least one embodiment of any one of methods (d-1) to (d-4), as disclosed herein, and the compound of Formula (IV) is converted to a compound of Formula (I) by at least one embodiment of method (e), as disclosed herein.

In another aspect of the invention, a compound of Formula (II) is converted to a compound of Formula (III) by at least one embodiment of method (c), as disclosed herein; the compound of Formula (III) is converted to a compound of Formula (IV) by at least one embodiment of any one of methods (d-1) to (d-4), as disclosed herein, and the compound of Formula (IV) is converted to a compound of Formula (I) by at least one embodiment of method (e), as disclosed herein.

In another aspect of the invention, a compound of Formula (VI) and a compound of Formula (VII) are converted to a compound of Formula (II) by at least one embodiment of method (b), as disclosed herein; the compound of Formula (II) is converted to a compound of Formula (III) by at least one embodiment of method (c), as disclosed herein; the compound of Formula (III) is converted to a compound of Formula (IV) by at least one embodiment of any one of methods (d-1) to (d-4), as disclosed herein, and the compound of Formula (IV) is converted to a compound of Formula (I) by at least one embodiment of method (e), as disclosed herein.

In another aspect of the invention, a compound of Formula (XI) and R⁷(CO)R⁸ are converted to a compound of Formula (II), wherein R³ is CHR⁷R⁸, by at least one embodiment of method (a), as disclosed herein; the compound of Formula (II) is converted to a compound of Formula (III) by at least one embodiment of method (c), as disclosed herein; the compound of Formula (III) is converted to a compound of Formula (IV) by at least one embodiment of any one of methods (d-1) to (d-4), as disclosed herein, and the compound of Formula (IV) is converted to a compound of Formula (I) by at least one embodiment of method (e), as disclosed herein.

In accordance with further aspect of the present invention, there is provided intermediate compounds of formulae (II), (III), (V) and (XIII) that are intermediates used in the instant method of preparing HIV RT inhibitor compounds of Formula (I).

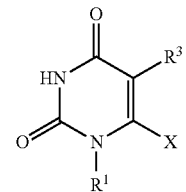

(II)

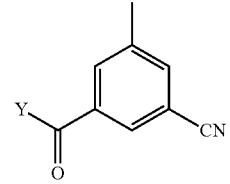

(III)

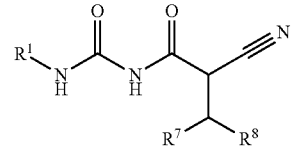

(V)

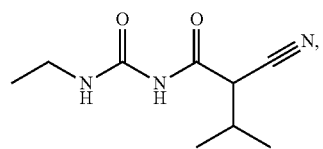

(VIII)

wherein

R¹, R³, R⁷ and R⁸ are defined as above; and

X is Cl, Br or I.

In one embodiment, the intermediate compounds comprise the compounds of formulae (i) to (v), or salts thereof:

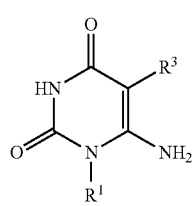

(i)

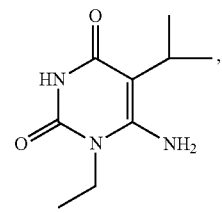

(ii)

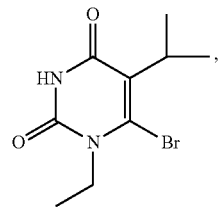

(iii)

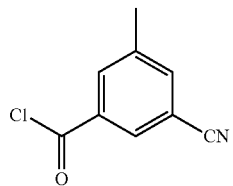

(iv)

-continued

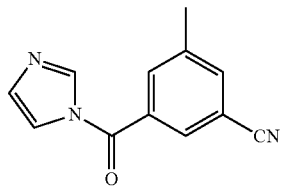

(v)

EXAMPLES

Exemplary methods for preparing the compounds of Formula (I) and intermediates are provided below. These methods are intended to illustrate the nature of such preparations and are not intended to limit the scope of applicable methods. While the examples specify certain reaction conditions, one skilled in the art will understand how to vary the specific reaction conditions to obtain the full scope of the invention.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example; boiling point and molecular weight for distillation and sublimation, presence or absence of polar functional groups for chromatography, stability of materials in acidic and basic media in multiphase extractions, and the like. One skilled in the art will apply techniques most likely to achieve the desired separation.

| List of abbreviations and acronyms | |
|---|---|
| Abbreviation | Meaning |
| ACN | acetonitrile |
| AcOH | acetic acid |
| AIBN | 2,2'-azobis(2-methylpropionitrile) |
| % AN | % area norm, i.e. % of total area under an integrated curve |
| Bn | benzyl |
| BnBr | benzylbromide |
| BSA | bis(trimethylsilyl)acetamide |

-continued

| List of abbreviations and acronyms | |
|---|---|
| Abbreviation | Meaning |
| BzCl | benzoyl chloride |
| CDI | carbonyl diimidazole |
| dba | dibenzylideneacetone |
| DCC | dicyclohexylcarbodiimide |
| DIPEA | di-isopropylethylamine |
| DMAP | 4-dimethylaminopyridine |
| DMA or DMAC | N,N-dimethylacetamide |
| DMTCl | dimethoxytrityl chloride |
| DMSO | dimethylsulfoxide |
| DMF | dimethylformamide |
| EtOAc | ethyl acetate |
| EtOH | ethanol |
| ESI | electrospray ionization |
| HMDS | hexamethyldisilazane |
| HPLC | High pressure liquid chromatography |
| LDA | lithium diisopropylamide |
| LRMS | low resolution mass spectrum |
| mCPBA | meta-chloroperbenzoic acid |
| MeOH | methanol |
| MTBE | methyl tertiary-butyl ether |
| m/z or m/e | mass to charge ratio |
| MH+ | mass plus 1 |
| MH− | mass minus 1 |
| MsOH | methanesulfonic acid |
| MS or ms | mass spectrum |
| NBS | N-bromosuccinimide |
| NMP | N-methylpyrrollidinone |
| psi | pounds per square inch |
| Pd/C | palladium on carbon |
| rt or r.t. | room temperature |
| TMSCl | chlorotrimethylsilane |
| TMSBr | bromotrimethylsilane |
| TMSI | iodotrimethylsilane |
| TEA | triethylamine |
| TBA | tributylamine |
| TBAP | tributylammonium pyrophosphate |
| TBSCl | t-butyldimethylsilyl chloride |
| TEAB | triethylammonium bicarbonate |
| TFA | trifluoroacetic acid |
| TLC or tlc | thin layer chromatography |
| δ | parts per million down field from tetramethylsilane |

Example 1

Preparation of 1-(2-cyano-3-methylbutanoyl)-3-ethylurea by a reductive alkylation of 1-(2-cyanoacetyl)-3-ethylurea

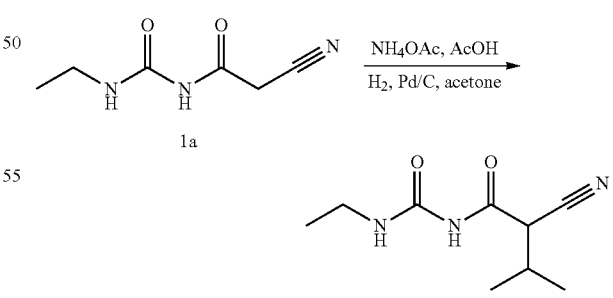

A Parr pressure reaction vessel* was charged with 1-(2-cyanoacetyl)-3-ethylurea (1a, 40 g, 0.258 mol), acetone (21.0 mL, 0.286 mol), acetic acid (3.0 mL, 0.052 mol), ammonium acetate (5.97 g, 0.077 mol), Pd/C (10 wt. %, Degussa E101 NE/W, 27.46 g, 0.013 mol) and EtOH (369 mL). The slurry was stirred vigorously at room temperature, and hydrogen gas was used to pressurize the bomb to 5-8 psi. The heterogeneous reaction mixture was stirred for ~24 h. Upon reaction completion, as determined by TLC analysis, the reaction mixture was filtered, the Pd/C washed with MeOH (5 vol.), and the filtrate was concentrated by 75%. To the reaction mixture was added 1-3 vol. of water and the white solids were then collected via filtration. The solids were washed with water and heptanes, and dried in a vacuum oven at 40° C., to yield 47.89 g (94%) of 1-(2-cyano-3-methylbutanoyl)-3-ethylure a 1.

$R_f$ (50% MTBE/heptanes) 0.59;

$^1$H NMR (400 MHz, CDCl$_3$) δ 10.36 (s, 1H), 8.21 (s, 1H), 3.46 (d, J=5.6 Hz, 1H), 3.35 (m, 2H), 2.40 (m, 1H), 1.21 (t, J=7.2 Hz, 3H), 1.14 (m, 6H).

* Note: This reaction works just as well under a normal balloon atmosphere of hydrogen.

Example 2

Preparation of Substituted Uracil 2 by a Cyclization of 1-(2-cyano-3-methylbutanoyl)-3-ethylurea 1

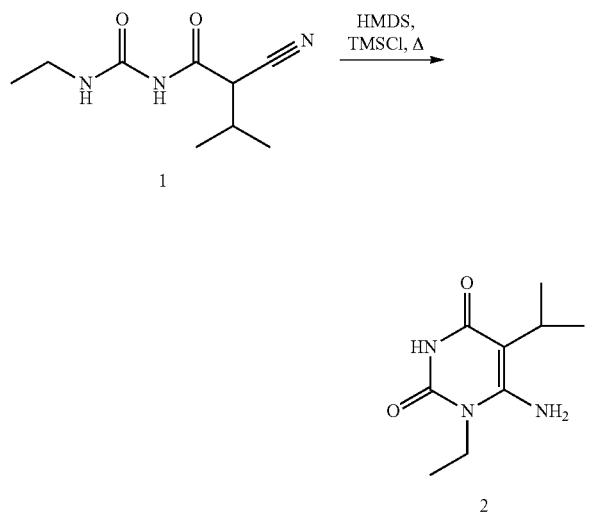

A flask was charged with 1-(2-cyano-3-methylbutanoyl)-3-ethylurea (1, 17.1 g, 87 mmol), HMDS (86 mL), and TMSCl (1.21 mL, 9 mmol). The reaction mixture is heated to reflux (125° C.) and left stirring for 16-24 h until solution became clear. Reaction is monitored by TLC and upon completion was cooled to room temperature then concentrated. To the resulting residue was added 1 vol. sat. NaHCO$_3$ solution in dropwise. The mixture was added 4-5 vol. of water along with 4-5 vol. of EtOAc. An emulsion forms as the two layers are combined and the slurry is filtered, and the solid is filtered and washed with water (2×0.25 vol) to afford an off-white solid. These solids were dried in a vacuum oven overnight at 40 to 50° C. to yield 7.25 g (42.4%) of 1-ethyl-5-isopropyl-6-amino uracil 2.

$R_f$ (25% EtOAc/hexanes) 0.52;

400 MHz $^1$H NMR (DMSO-d6) δ 10.19 (s, 1H), 3.82 (q, J=6.83 Hz, 2H), 3.79 (septet, J=6.83 Hz, 1H), 1.19-1.04 (m, 9H).

Example 3

Preparation of Substituted Uracil 2 by a Condensation/Cyclization of Ethyl Urea 3a and Ethyl 2-cyano-3-methylbutanoate 3b

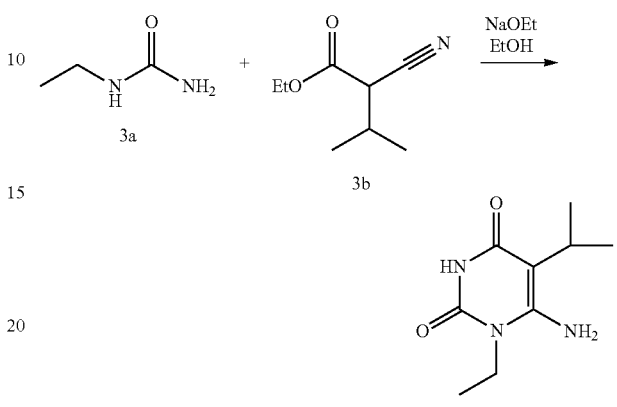

A flask was charged with ethyl 2-cyano-3-methylbutanoate (3b, 10.0 g, 64.4 mmol), ethyl urea (3a, 5.96 g, 67.6 mmol) and EtOH (129 mL). To the slurry at room temperature was added sodium ethoxide in ethanol (21% w/w soln, 28.8 mL), mild exotherm detected. The heterogeneous reaction mixture was then heated to reflux. The reaction was refluxed for 4 to 12 h. Upon reaction completion, as determined by TLC analysis, the reaction mixture was concentrated and solvent exchanged to acetonitrile (ACN) through 3×20 mL co-evaporations leaving a basic 1-2 vol. solution in ACN. To the reaction mixture was added 1-2 vol. of water followed by a pH adjustment with 2N HCl (aq.). As the pH approached 10 white to off-with solids began forming and as the pH was further reduced to 9 (by pH paper) white slurry resulted. This slurry was aged for 0.5-24 h and then filtered. The resulting solids were washed with 1 vol. of water and 2×2 vol. MTBE. The white to off-white solids were then dried in a vacuum oven at 40-50° C. giving 4.99 g (39%) of 1-ethyl-5-isopropyl-6-amino uracil 2:

$R_f$ (EtOAc) 0.3;

400 MHz $^1$H NMR (DMSO-d6) δ 10.19 (s, 1H), 6.32 (s, 2H), 3.83 (q, J=6.8 Hz, 2H), 2.79 (septet, J=6.8 Hz, 1H), 1.15 (d, J=6.8 Hz, 6H), 1.07 (t, J=6.8 Hz, 3H);

100 MHz $^{13}$C NMR (DMSO-d6) δ 162.3, 151.6, 150.9, 91.1, 36.9, 25.0, 21.0 (2), 14.0.

Example 4a

Preparation of Substituted Uracil 2 by an Alternative Condensation/Cyclization of Ethyl Urea 3a and ethyl 2-cyano-3-methylbutanoate 3b A flask was charged with ethyl 2-cyano-3-methylbutanoate (3b, 20.72 g, 133.5 mmol), ethyl urea (3a, 12.35 g, 140.2 mmol) and MeOH (97.2 mL). To the slurry at room temperature was added sodium methoxide in methanol (25% w/w soln, 36.8 mL), mild exotherm detected. The heterogeneous reaction mixture was then heated to reflux. The reaction was refluxed for 4-12 h. Upon reaction completion, as determined by TLC analysis, the reaction mixture was concentrated and solvent exchanged to acetonitrile (ACN) through 3×50 mL co-evaporations leaving a basic 1-2 vol. solution in ACN. To the reaction mixture was added 1-2 vol. of water followed by a pH adjustment with 2N HCl (aq.). As the pH approached 10, white to off-with solids began forming and, as the pH was further reduced to 3 to 4, (by pH paper) white slurry resulted. This slurry was aged for 0.5 to 24 h and then filtered. The resulting solids were washed with 1 vol. of water and 2×2 vol. MTBE. The white to off-white solids were then dried in a vacuum oven at 40 to 50° C. giving 18.63 g (60%) of 1-ethyl-5-isopropyl-6-amino uracil 2 (HCl salt).

$R_f$ (EtOAc) 0.3;
400 MHz $^1$H NMR (DMSO-d6) δ 10.17 (s, 1H), 6.31 (s, 2H), 3.81 (q, J=6.8 Hz, 2H), 2.77 (septet, J=6.8 Hz, 1H), 1.13 (d, 6H), 1.05 (t, 3H);
100 MHz $^{13}$C NMR (DMSO-d6) δ 162.3, 151.6, 150.9, 91.1, 36.9, 25.0, 21.0 (2), 14.0.

* The sulfuric acid ($H_2SO_4$), hydrobromic acid (HBr), and phosphoric acid ($H_3PO_4$) salts of 2 were prepared by the same method by substituting the respective acids for the HCl.

Example 4b

Preparation of Substituted Uracil 2 by an Alternative Condensation/Cyclization of Ethyl Urea 3a and Ethyl 2-cyano-3-methylbutanoate 3b A flask was charged with ethyl 2-cyano-3-methylbutanoate (3b, 143.1 g, 0.921 mol), and ethyl urea (3a, 89.28 g, 1.010 mol). To the flask at room temperature was added sodium ethoxide in ethanol (21% w/w soln, 417.6 mL), mild exotherm detected. The heterogeneous reaction mixture was then heated to reflux. The reaction was refluxed for 6 to 12 h. Upon reaction completion, as determined by TLC analysis, the reaction mixture was concentrated and solvent exchanged to acetonitrile (ACN) through 3×200 mL co-evaporations leaving a basic 1-2 vol. solution in ACN. To the reaction mixture was added 1 to 2 vol. of water followed by a pH adjustment with 2N HCl (aq.). As the pH approached 10 white to off-with solids began forming and as the pH was further reduced to 2 (by pH paper), a white slurry resulted of the HCl Salt. This slurry was aged for 0.5-24 h and then filtered. The resulting solids were washed with 1 vol. of water and 2×2 vol. MTBE. The white to off-white solids were then dried in a vacuum oven at 40-50° C. giving 134.1 g (62%) of 2.

$R_f$ (EtOAc) 0.3;
400 MHz $^1$H NMR (DMSO-d6) δ 10.19 (s, 1H), 6.32 (s, 2H), 3.83 (q, J=6.8 Hz, 2H), 2.79 (septet, J=6.8 Hz, 1H), 1.15 (d, J=6.8 Hz, 6H), 1.07 (t, J=6.8 Hz, 3H);
100 MHz $^{13}$C NMR (DMSO-d6) δ 162.3, 151.6, 150.9, 91.1, 36.9, 25.0, 21.0 (2), 14.0.

Example 5

Diazotization/Bromination of Substituted Uracil 2

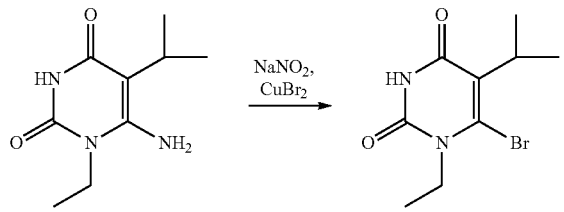

A flask was charged with the HCl salt of 2 (10.05 g, 43.01 mmol), NaNO$_2$ (4.466 g, 64.72 mmol) and CuBr$_2$ (19.25 g, 86.18 mmol). To the solids at room temperature was added a 1:1 mixture of acetonitrile/water (100 mL), during which steady bubbling was observed. Over the next 16 min the temperature of the heterogeneous reaction mixture increased by 10° C., peaking at 32° C. The reaction was left to stir overnight. To the reaction mixture was added ethyl acetate (100 mL) and 1N sulfuric acid (100 mL). The aqueous layer was removed and to the organics was added 1N sulfuric acid (50 mL). The aqueous layer was removed and the organics were washed with 18% brine (50 mL) followed by a solvent swap for diisopropyl ether. The organics were concentrated and the resulting solid was slurried with diisopropyl ether (20 mL) for 30 minutes. The solid was then filtered and washed with diisopropyl ether (2×5 mL) and dried giving an off-white solid 5 (9.02 g, 80%).

$R_f$ (40% ethyl acetate/hexanes) 0.48;
400 MHz $^1$H NMR (DMSO-d6) δ 11.48 (s, 1H), 4.05 (q, J=6.83 Hz, 2H), 3.10 (septet, J=6.83 Hz, 1H), 1.21-1.15 (m, 9H);
100 MHz $^{13}$C NMR (DMSO-d6) δ=160.2, 149.1, 135.5, 118.9, 44.1, 32.3, 19.5 (2), 13.8.

Example 6

Preparation of Electrophile 6a or 6b from Carboxylic Acid 6

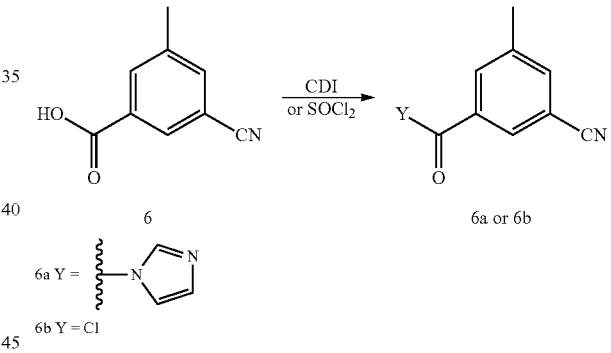

Imidazolide 6a: To a 250 mL round bottom flask was charged carboxylic acid 6 (10 g, 0.062 mol), CDI (10.54 g, 0.065 mol), and THF (62 mL) at rt. The initial reaction/dissolution is endothermic in nature. The reaction mixture was allowed to stir for ~19 h where the resulting solids were filtered off and washed with 5 vol. water and 20 vol. MTBE. The white solids were placed in a vacuum oven at 40° C. to be dried. Resulting dried solids, 6a, were pure by $^1$H NMR and were used without further purification (12.18 g isolated, 93.0% yield). (Note: Compound 6a can be recrystallized from 4 vol. THF and 4 vol. heptanes.)

$^1$H-NMR (400 MHz, acetone) δ 8.16 (1H, s), 8.07 (1H, s), 8.00 (1H, s), 7.97 (1H, s), 7.66 (1H, s), 7.13 (1H, s), 2.55 (3H, s);
$^{13}$C NMR (100 MHz, acetone) δ 205.5, 166.7, 140.2, 135.7, 135.3, 134.6, 134.3, 130.3, 121.3, 118.3, 112.5, 20.3.

Acid Chloride 6b: To a 100 mL round bottom flask was charged 6 (10 g, 0.062 mol) and SOCl$_2$ (31 mL) at rt. The reaction mixture was then heated to reflux. After ~30 min. all solids had dissolved and the reaction mixture was allowed to reflux for another 30 min. At that time the reaction was cooled to rt and stirred for 1 h. The reaction mixture as then concentrated to dryness and a white to off white solid remained in the flask. These solids were dried under vacuum without heat. Resulting dried solids, 6b, were pure by $^1$H NMR and were used without further purification (11.01 g isolated, 98.8% yield).

$^1$H-NMR (400 MHz, CDCl$_3$) δ 8.21 (1H, s), 8.14 (1H, s), 7.70 (1H, s), 2.49 (3H, s).

Example 7

Preparation of Compound 7 by Coupling Bromide 5 with Imidazolide 6a or Acid Chloride 6b

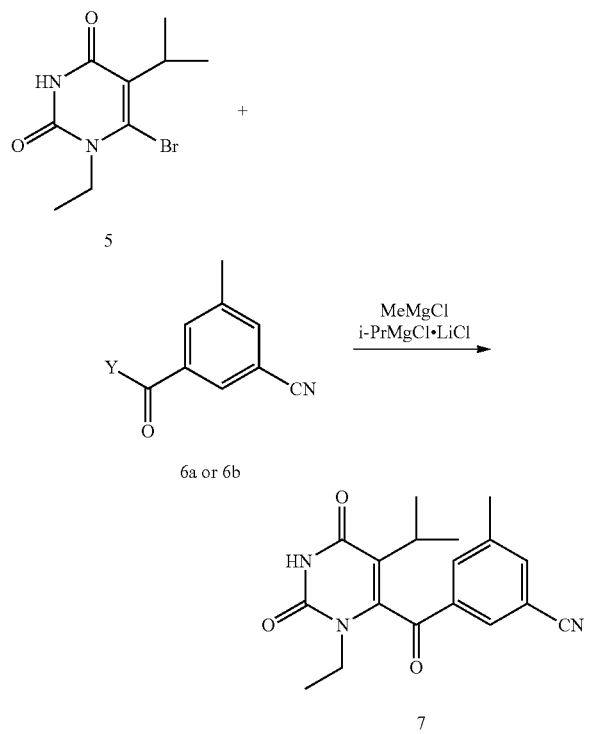

Coupling of 5 and Imidazolide 6a: To a 25 mL round bottom flask under N$_2$ (g) was charged bromide 5 (325 mg, 1.24 mmol) and THF (dry, 2.5 mL) at rt. The reaction mixture was then cooled to −20° C. where MeMgCl (22% w/w in THF, 0.44 mL) was charged. Off gassing was evident upon addition of the Grignard reagent and the reaction was exothermic. The reaction was allowed to stir for ~30 min. where i-PrMgCl.LiCl (TurboGrignard, 14% w/w in THF, 1.13 mL) was then charged dropwise. After ~30 min the reaction was sampled for TLC analysis. The TLC showed no bromide 5. In a separate flask the imidazolide 6a (389 mg, 1.84 mmol) was dissolved in 2 mL of dry THF. The imidazolide solution was then charged dropwise to the reaction mixture at −20° C. which was also exothermic in nature. After ~30 min the reaction was warmed to −5° C. and then sampled for TLC analysis. The TLC indicated that the reaction was not complete so the reaction was allowed to stir for another hour. At that time the reaction was quenched with 2 N HCl (aq.) to pH ~2 and the layers were allowed to separate. The aq. layer was then extracted with EtOAc (2×10 mL) then all of the organic layers were combined and extracted with 20% w/w NaCl (aq.) (10 mL). The organics were then concentrated to dryness and the off-white solids were taken up in a minimal amount of THF and purified by silica gel chromatography to yield 225.7 mg of pure 7 (56% yield).

$^1$H-NMR (400 MHz, CDCl$_3$) δ 9.24 (1H, s), 8.01 (1H, s), 7.93 (1H, s), 7.77 (1H, s), 3.88 (1H, m), 3.14 (1H, m), 2.52 (3H, s), 2.20 (1H, m), 1.22-1.11 (9H, m);

$^{13}$C NMR (100 MHz, acetone) δ 188.6, 162.3, 150.5, 145.8, 141.7, 139.0, 135.5, 133.9, 130.3, 117.4, 116.9, 114.4, 41.9, 29.4, 21.4, 20.5, 19.8, 14.3.

Coupling of 5 and Acid Chloride 6b: To a 25 mL round bottom flask under N$_2$ (g) was charged bromide 5 (1 g, 3.83 mmol) and THF (dry, 8 mL) at rt. The reaction mixture was then cooled to −5° C. where MeMgCl (22% w/w in THF, 1.4 mL) was charged. Off gassing was evident upon addition of the Grignard reagent and the reaction was exothermic. The reaction was allowed to stir for ~30 min. where i-PrMgCl.LiCl (TurboGrignard, 14% w/w in THF, 3.2 mL) was then charged dropwise. After ~30 min the reaction was sampled for TLC analysis. The TLC showed no bromide 5. In a separate flask the acid chloride 6b (826 mg, 4.60 mmol) was dissolved in 1 mL of dry THF. The acid chloride solution was then charged dropwise to the reaction mixture at −5° C. which was also exothermic in nature. After ~30 min the reaction was warmed to 10° C. and then sampled for TLC analysis. The TLC indicated that the reaction was not complete so the reaction was allowed to stir for another 3 h. At that time the reaction was quenched with 2 N HCl (aq.) to pH ~2 and the layers were allowed to separate. The aq. layer was then extracted with EtOAc (2×20 mL) then all of the organic layers were combined and extracted with 20% w/w NaCl (aq.) (20 mL). The organics were then concentrated to dryness and the off-white solids were taken up in a minimal amount of THF and purified by silica gel chromatography to yield 722.5 mg of pure 7 (58% yield).

$^1$H-NMR (400 MHz, CDCl$_3$) δ 9.25 (1H, s), 8.03 (1H, s), 7.95 (1H, s), 7.79 (1H, s), 3.89 (1H, m), 3.12 (1H, m), 2.51 (3H, s), 2.20 (1H, m), 1.24-1.11 (9H, m).

While the invention has been described with respect to the above specific embodiments, it should be recognized that various modifications and changes may be made to the invention by those skilled in the art which also fall within the scope of the invention as defined by the appended claims.

What is claimed is:

1. A method of preparing a compound of Formula (I), which comprises subjecting a compound of Formula (IV) to a reaction with a compound of Formula (V):

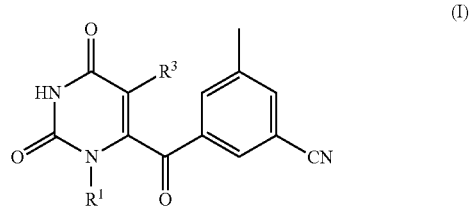

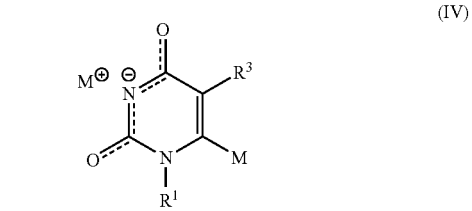

(V)

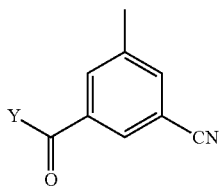

(II)

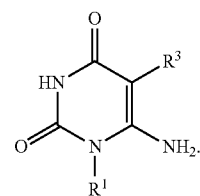

wherein,

R¹ is alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, heterocyclyl, substituted heterocyclyl, arylalkyl, substituted arylalkyl, heteroarylalkyl, or substituted heteroarylalkyl;

R³ is H, alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, heterocyclyl, substituted heterocyclyl, arylalkyl, substituted arylalkyl, heteroarylalkyl, substituted heteroarylalkyl or —CHR⁷R⁸, R⁷ and R⁸ being each independently H, alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, heterocyclyl, substituted heterocyclyl, arylalkyl, substituted arylalkyl, heteroarylalkyl, or substituted heteroarylalkyl;

M is MgX¹ or Li, X¹ being halogen; and

Y is selected from the group consisting of halogen, cyano, imidazol-1-yl, pyrazol-1-yl, —O—C(O)R² or —O—C(O)OR⁴, R² being H, alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, arylalkyl, substituted arylalkyl, heteroarylalkyl, or substituted heteroarylalkyl, and R⁴ being alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, arylalkyl, substituted arylalkyl, heteroarylalkyl, or substituted heteroarylalkyl.

2. The method of claim 1, wherein Y is imidazol-1-yl or halogen.

3. The method of claim 1, wherein M is MgX¹.

4. The method of claim 1, wherein the compound of Formula (IV) is prepared by treating a compound of Formula (III) with an organomagnesium or organolithium reagent:

(III)

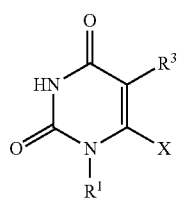

wherein
X is Cl, Br or I.

5. The method of claim 4, wherein X is Br or I.

6. The method of claim 4, wherein the compound of Formula (III) is prepared by treating a compound of Formula (II) with a nitrosating reagent in the presence of a transition metal halide:

7. The method of claim 6, wherein the nitrosating reagent is selected from the group consisting of alkali metal nitrite, alkaline earth nitrite, and nitrite ester having alkyl group or substituted alkyl group.

8. The method of claim 6, wherein the transition metal halide is selected from the group consisting of a transition metal chloride, bromide, iodide and a mixture thereof.

9. The method of claim 8, wherein the transition metal halide is CuBr₂.

10. The method of claim 6, wherein the compound of Formula (II) is prepared by subjecting a compound of Formula (VI) to a reaction with a compound of Formula (VII) in the presence of a base:

(VI)

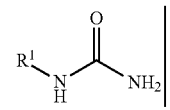

(VII)

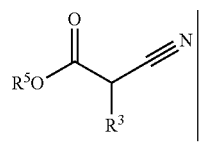

wherein:

R⁵ is alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, heterocyclyl, substituted heterocyclyl, arylalkyl, substituted arylalkyl, heteroarylalkyl, substituted heteroarylalkyl or Si(R⁶)₃, R⁶ being each independently alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, heterocyclyl, substituted heterocyclyl, arylalkyl, substituted arylalkyl, heteroarylalkyl, or substituted heteroarylalkyl.

11. The method of claim 10, wherein the base is an alkali metal alkoxide.

12. The method of claim 6, wherein R³ is CHR⁷R⁸ and the compound of Formula (II) is prepared by (a-1) treating a compound of Formula (XI) with a compound selected from the group consisting of the compounds of formulae (XII) to (XIV) in the presence of a reducing agent thereby forming a compound of Formula (VIII), and (a-2) treating the compound of Formula (VIII) with the compound of Formula (IX) in the presence of the compound of Formula (X):

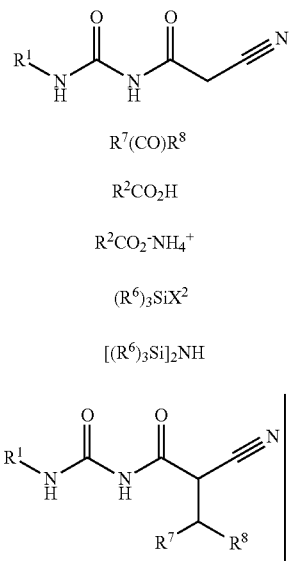

(XI)
(XII)
(XIII)
(XIV)
(IX)
(X)
(VIII)

wherein $R^6$ is alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, heterocyclyl, substituted heterocyclyl, arylalkyl, substituted arylalkyl, heteroarylalkyl, or substituted heteroarylalkyl $X^2$ is halogen.

13. The method of claim 12, wherein the reducing agent comprises a catalyst selected from the group consisting of a transition metal, a noble metal and palladium on carbon; and $H_2$.

14. The method of claim 12, wherein each $R^6$ is methyl and $X^2$ is Cl.

15. The method of claim 1, wherein each $R^7$ and $R^8$ is alkyl.

16. The method of claim 1, wherein each $R^1$ and $R^3$ is alkyl.

17. The method of claim 16, wherein $R^1$ is ethyl.

18. The method of claim 16, wherein $R^3$ is isopropyl.

* * * * *